United States Patent [19]

Römisch et al.

[11] Patent Number: 5,589,395

[45] Date of Patent: Dec. 31, 1996

US005589395A

[54] METHOD FOR STABILIZING ANNEXINS

[75] Inventors: Jürgen Römisch; Bernhard Auerbach; Hermann Pelzer, all of Marburg, Germany

[73] Assignee: Behringwerke Aktiengesellschaft, Marburg, Germany

[21] Appl. No.: 46,908

[22] Filed: Apr. 15, 1993

Related U.S. Application Data

[63] Continuation of Ser. No. 629,718, Dec. 18, 1990, abandoned.

[30] Foreign Application Priority Data

Dec. 20, 1989 [DE] Germany ............. 39 42 081.7

[51] Int. Cl.⁶ ............. G01N 33/92; G01N 11/00
[52] U.S. Cl. ............. 436/71; 436/87; 436/176; 436/15; 436/18; 435/792; 530/399
[58] Field of Search ............. 435/1, 2, 7.92; 436/15, 8, 18, 71, 87, 176; 514/12, 21; 530/399

[56] References Cited

U.S. PATENT DOCUMENTS

| | | | |
|---|---|---|---|
| Re. 32,874 | 2/1989 | Rock et al. ............. | 424/101 |
| 4,409,334 | 10/1983 | Lill et al. ............. | 436/8 |
| 4,820,689 | 4/1989 | Ikuzawa et al. ............. | 435/71.1 |
| 4,937,324 | 6/1990 | Fujikawa et al. ............. | 530/350 |
| 4,994,367 | 2/1991 | Bode et al. ............. | 435/2 |
| 5,217,954 | 6/1993 | Foster et al. ............. | 514/12 |

FOREIGN PATENT DOCUMENTS

0040799A3  12/1981  European Pat. Off. .

OTHER PUBLICATIONS

The Merck Index, pp. 672–673, Item 4543, (1983).

Bohn, H., et al., "New Placental Proteins and Their Potential Diagnostic Significance as Tumour Markers," Oncodevelopmental Biology and Medicine, 2: 141–153 (1981).

Roemisch, J., et al., "Annexins: Calcium–Binding Proteins of Multi–Functional Importance?" Medical Microbiology and Immunology, 180: 109–126 (1991).

Gőcze, P. M. et al., Med. Sci. Res., 16: 407–408 (1988).

Prowse, C. et al., Thromb. Res., 25: 219–227 (1982).

*Primary Examiner*—Robert J. Warden
*Assistant Examiner*—N. Bhat
*Attorney, Agent, or Firm*—Finnegan, Henderson, Farabow, Garrett & Dunner, L.L.P.

[57] ABSTRACT

A method for stabilizing the functional activity of annexins in a biological fluid sample is provided.

7 Claims, No Drawings

METHOD FOR STABILIZING ANNEXINS

This application is a continuation, of application Ser. No. 07/629,718, filed Dec. 18, 1990, now abandoned.

The invention relates to an agent for stabilizing the functional activity of annexins and to suitable components for collecting body fluids for the quantitative determination thereof.

Inter alia the proteins PP4, PP4-X, PAP III, p68, anchorin and lipocortin I and II are referred to as annexins or else lipocortins or calpactins. Their physiological role has not yet been completely clarified.

Annexins have been found in many species, human organs and various cell types. They have, according to present knowledge, a large anti-inflammatory or anticoagulatory potential, but these proteins are present only in very low concentrations in body fluids, in particular in the blood (1–5 ng/ml). However, as has been shown using PP4 as an example, they can often be detected in highly increased concentrations in body fluids, for example in blood plasma, with certain diseases and can therefore have substantial clinical relevance as markers for an early detection or for following the course of a disease (Gocze, P.M. et al. (1988) Med. Sci. Res. 16, 407–408). This holds just as true for the proteins PP4-X, PAP III, p68, anchorin and lipocortin I and II. The proteins can be quantitatively determined by means of sensitive detection methods, such as, for example, RIA or ELISA.

Decisive for the significance of a test is the normal range, which gives the concentration of the particular analyte in body fluids of a reference group composed of healthy test persons, in comparison with the pathological range. This defines an upper limit of the normal range, which is also referred to as cut-off. In test methods such as RIA or ELISA which are very sensitive, the way of obtaining the body fluids is, inter alia, also of great importance since, for example, the cellular components of blood might be damaged during its collection and the test results might be falsified by this. Often undesirable side effects, such as too high a background during the determination later on, can be avoided by careful veni-puncture and rapid mixing of the fluid to be collected with additives protecting the substance to be determined. A known type of agent for taking blood is citrate which prevents clotting by binding calcium ions in a complex.

However, as an agent for stabilizing samples, citrate has the disadvantage that the samples obtained by admixing this agent are not suitable for quantifying the annexins (Table 1). Exemplary tests carried out on PP4 showed that the PP4 concentrations, determined by ELISA, in plasmas which were derived from whole blood of 10 healthy donors to which citrate had been added as anticoagulant were between 2 and 8 ng/ml and varied to a degree which cannot be tolerated for a test of this kind. EDTA plasmas did not lead to satisfactory results either since it was impossible to define an acceptable upper limit with this chelate-forming agent and wide variations occurred in healthy donors.

The present invention thus had the object of finding an agent for stabilizing the functional activity of the annexins, which agent makes it possible to carry out a reliable quantification of the annexins in body fluids.

According to the invention, an agent for stabilizing the functional activity of annexins is now used for sampling, which agent contains an anticoagulant, a chelate-forming agent and one or a combination of two or more of the class of the aggregation inhibitors, which is known per se to those skilled in the art, such as, for example, chloroquine, hydroxychloroquine, quinacrine, camoquine, dibucaine, lidocaine, procaine, tetracaine, trifluoperazine, reserpine, acetylsalicylic acid, indomethazine, poquazone, prenylamine lactate, perhexiline maleate, nifedipine, verapamil and/or pentoxifylline.

The definition of a reference range and a sufficiently low cut-off for the determination of the annexins is made possible by this.

In the test mixture, the aggregation inhibitors are used in concentrations of 0.2–200 mmol/l, preferably of 2–200 mmol/l, very particularly preferably of 5–50 mmol/l.

It is known of aggregation inhibitors that they more or less efficiently inhibit the aggregation of blood platelets and the release of, for example, the e-granules which contain platelet factor (PF4) (Prowse, C. et al. (1982) Thromb. Res. 25, 219–227). It can be said, without intending to specify a way of action, that the invention described above is not based on an inhibition of the α-granule release, however, since, despite strongly varying PF4 values, no correlation with the determined PP4 values can be seen (Table 1). Optimum "normal" PP4 values are achieved only with the agent according to the invention.

In one procedure, a body fluid, for example blood, during or a short time after withdrawal, is mixed with an agent which is present in a concentration such that the mixture of agent and sample contains 0.2–500 mmol, preferably 2–200mmol, very particularly preferably 5–50mmol of a chelate-forming agent, for example EDTA, EGTA or a salt of citric acid or oxalic acid and 100–100,000 units, preferably 500–50,000 units, of an anticoagulant, such as, for example, heparin, hirudin, chondroitin sulfate, dermatan sulfate or a pentosan polysulfate, and 2–200 mmol of one or more of the abovementioned aggregation inhibitors per liter, and the cellular components are, if present, separated from the fluid. All three, the chelate-forming agents, the anticoagulants and the additives can, in each case, be used on their own, combined or together in the described combination. This procedure is suitable for the quantitative determination both of PP4 and the other annexins PP4-X, PAP III, p68, anchorin, lipocortin I and II.

In a preferred procedure, nine parts of a body fluid are mixed with one part of a solution which contains 2–200 mmol/l EDTA, 5000–50,000 units/l heparin and 5–50 mol/l of at least one of the substances chloroquin, hydroxychloroquin and quinacrin, and the cellular components are, if present, separated from the fluid.

Anticoagulants are compounds known per se to those skilled in the art, such as, for example, hirudin, heparin, dermatan sulfate or pentosan sulfate, heparin and hirudin being particularly preferred. The substances referred to as chelate-forming agents here, which are known per se to those skilled in the art, such as, for example, citrate, oxalate, EDTA or EGTA, EDTA or EGTA being preferred, also have anticoaqulatory action.

The optimum concentrations are known per se to those skilled in the art.

Agents such as those described for medium C in Example 1 are very much preferred.

The following examples are intended to illustrate the invention:

EXAMPLE 1

Sampling

A back pressure of about 40 mm Hg was generated on the upper arm of healthy blood donors and, after exact venipuncture using a "butterfly" cannula, 4.5 ml of whole blood were drawn into a disposable syringe into which 0.5 ml of withdrawal medium had been initially introduced. The following solutions were used as withdrawal media:

Medium A: 110 mmol/l trisodium citrate solution

Medium B: 27 mmol/l EDTA solution with 0.9% NaCl added, pH 7.4

Medium C: 134 mmol/l EDTA solution with 20,000 units of heparin/l and 16 mmol/l hydroxychloroquin sulfate added, pH 7.4

The samples were then immediately transferred into polystyrene tubes and, until their further processing, stored at +2° to +8° C. for at least 30 min, but a maximum of 2 hours.

The cooled samples were centrifuged at 2000×g for 15 min and the plasma supernatant was centrifuged for a further. 15 min at 8000×g. Plasma supernatants were used for measurement in the PP4 enzyme immunoassay. The samples provided with withdrawal medium C were additionally tested in the PF4 immunoassay.

PF4 and PP4 Immunoassays

The PF4 concentration of the samples provided with the withdrawal medium C was determined by the Enzygnost platelet factor 4 enzyme immunoassay (OULV, Behringwerke) in accordance with the instructions for the test. In order to measure the PP4 concentration, the test-specific components described further below and reagents from commercially available test kits of Behringwerke were used: 100 µl of standard (0.3 to 10 µg/1; Batch No. 268907, BW) or 100 µl of plasma samples diluted 1:2 or 1:11 with the TAT sample buffer (OURG, BW), in each case, were pipeted into the wells of microtiter plates (Nunc) which were coated with polyclonal anti-PP4 antibodies (from rabbits, Batch No. 278905, BW) and were incubated at 37° C. for 2 hours. After washing three times with the diluted Enzygnost washing buffer (OSEW, BW), 100 µl of an anti-PP4 antibody/peroxidase conjugate solution (Batch No. 308808, BW) were introduced into each individual well. The following two-hour incubation step at 37° C. was completed by a washing cycle repeated three times. For the third incubation step (room temperature) 100 µl of a buffer/substrate chromogen solution (TMB; OUVG/OUVF, BW) in each case were then pipeted into the wells and the enzyme reaction was stopped after 30 rain with Enzygnost stop solution (OSFA, BW). The extinction of the standards and samples was determined at 450 nm and the PP4 concentration calculated, allowing for the dilution factor, by means of the plotted standard curve.

Result

The lowest PP4 concentrations were measured in the plasma samples provided with the withdrawal medium C. In medium B and especially in Medium A distinctly higher PP4 values which strongly varied from test person to test person were found (Tab. 1).

TABLE 1

Tab. 1: PF4 and PP4 values measured in various plasma samples (from 10 healthy blood donors)

| Withdrawal medium: | PF4 (µg/l) | PP4 (µg/l) | | |
|---|---|---|---|---|
| | C | A | B | C |
| Blood donor: | | | | |
| 1 | 3.7 | 5.1 | 1.0 | 1.9 |
| 2 | 3.5 | 4.5 | 1.5 | 0.7 |
| 3 | 8.7 | 7.6 | 5.3 | 1.2 |
| 4 | 2.4 | 4.4 | 0.8 | 1.0 |
| 5 | 3.2 | 2.0 | 1.9 | 0.7 |
| 6 | 6.4 | 2.8 | 1.8 | 0.7 |
| 7 | 3.9 | 8.0 | 1.7 | 0.9 |
| 8 | 2.5 | 3.3 | 1.0 | 0.7 |
| 9 | 4.2 | 2.4 | 1.4 | 1.0 |
| 10 | 4.4 | 2.0 | 0.9 | 1.1 |

EXAMPLE 2

In order to ensure that the withdrawal media do not interfere with the recovery of PP4 in the enzyme immunoassay, 5.5 ng of standard PP4 were, simultaneously with the sample buffer, added during the 1:11 dilution of the plasma samples.

The PP4 recovery rate was approximately identical in the case of all withdrawal media (Tab. 2) so that, in blood withdrawal, exclusively the method and the choice of the suitable withdrawal medium are the reasons for an increased PP4 level in normal healthy persons.

TABLE 2

Tab. 2: Recovery rate of PP4 (%) in various plasmas (n = 10)

| Medium A: | 87.0 +/− 9.2% |
|---|---|
| Medium B: | 87.5 +/− 7.5% |
| Medium C: | 87.8 +/− 6.7% |

We claim:

1. A method for stabilizing annexins in a biological fluid sample comprising the steps of:

(a) obtaining the biological fluid sample; and (b) bringing said sample into contact with an agent containing an anticoagulant, a chelate-forming agent and at least one aggregation inhibiting substance, said aggregation inhibiting substance selected from the group consisting of chloroquine, hydroxychloroquine, quinacrine, camoquine, dibucaine, lidocaine, procaine, tetracaine, chlorpromazine, trifluoparazine, reserpine, acetylsalicyclic acid, indomethacin, poquazone, prenylamine lactate, perhexiline maleate, nifedipine, verapamil and pentoxifylline.

2. The method as claimed in claim 1, wherein the concentration of the aggregation inhibitor(s) is 2–200 mmol/l.

3. The method as claimed in claim 1, wherein said aggregation inhibiting substance is selected from the group consisting of chloroquine, hydroxychloroquine and quinacrine.

4. The method as claimed in claim 1, wherein said anticoagulant is one or more anticoagulants selected from the group consisting of hirudin, heparin, dermatan sulfate, chondroitin sulfate and a pentosan polysulfate in a concentration of 100–100,000 units per liter.

5. The method as claimed in claim 1, wherein the anticoagulant is heparin in a concentration of 5000–50,000 units per liter.

6. The method as claimed in claim 1, wherein said chelate-forming agent is one or more chelate-forming agents in a concentration of 0.2–500 mmol/l selected from the group consisting of a salt of citric acid, a salt of oxalic acid, EDTA and EGTA.

7. The method as claimed in claim 1, wherein the chelate forming agent is EDTA in a concentration of 2–200 mmol/l.

* * * * *